US006184211B1

(12) United States Patent
Szyf

(10) Patent No.: US 6,184,211 B1
(45) Date of Patent: *Feb. 6, 2001

(54) INHIBITION OF DNA METHYLTRANSFERASE

(75) Inventor: Moshe Szyf, Montréal (CA)

(73) Assignee: MethylGene Inc., Quebec (CA)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 08/652,425

(22) PCT Filed: Nov. 30, 1994

(86) PCT No.: PCT/CA94/00659

§ 371 Date: May 30, 1996

§ 102(e) Date: May 30, 1996

(87) PCT Pub. No.: WO95/15373

PCT Pub. Date: Jun. 8, 1995

(30) Foreign Application Priority Data

Nov. 30, 1993 (CA) .................................................. 2110213
Jul. 7, 1994 (GB) .................................................. 9413680

(51) Int. Cl.[7] ........................ A61K 48/00; A61K 39/395; C07H 21/04; C12Q 1/68
(52) U.S. Cl. ........................ 514/44; 536/24.5; 424/130.1; 435/6; 435/7.1; 435/183
(58) Field of Search .................................. 536/23.1, 24.5; 514/44; 424/130.1; 435/183

(56) References Cited

U.S. PATENT DOCUMENTS 5,919,772 * 7/1999 Szyf et al. .............................. 514/44
6,020,318 * 2/2000 Szyf et al. .............................. 514/44

FOREIGN PATENT DOCUMENTS

WO 92/06985 4/1992 (WO) .
WO 92/15680 9/1992 (WO) .

OTHER PUBLICATIONS

Rojanasakul, Antisense oligonucleotide therapeutics: drug delivery and targeting, Advanced Drug Delivery Reviews, vol.18, pp. 115–131, 1996.*
Miller et al., Gene transfer and antisense nucleic acid techniques, Parasitology Today, vol. 10(3), pp. 92–97, 1994.*
Gura, Antisense has growing pains, Science, vol. 270, pp. 575–577, Oct. 1995.*
Wu–Pong, Oligonucleotides: opportunities for drug therapy and research, Pharmaceutical Technology, vol. 18, pp. 102–114, Oct. 1994.*
Stull et al, Antigene, ribozyme, and aptamer nucleic acid drugs: progress and prospects, Pharmaceutical Research, vol. 12(4), pp. 465–483, 1995.*
Wagner, Gene inhibition using antisense oligonucleotides, Nature, vol. 372, pp. 333–335, Nov. 1994.*
Stein et al., Antisense oligonucleotides as therapeutic agents—Is the bullet realy magical?, Science, vol. 261, pp. 1004–1012, Aug. 1993.*
Weiss, Upping the antisense ante, Science News, vol. 139, pp. 108–109, 1991.*
Benz, Clinical management of gene expression, N.E. J. Med., vol. 307(24), pp. 1515–1516, Dec. 1982.*
Gewirtz et al., Facilitating oligonucleotide delivery: Helping antisense deliver on its promise, Proc. Natl. Acad. Sci., vol. 93, pp. 3161–3163, Apr. 1996.*
Branch, A good antisense is hard to find, TIBS, vol. 23, pp. 45–50, Feb. 1998.*
Golden, Of mice and men: Don't blame the rodents, Time, vol. 151 (19), p. 44, May 18, 1998.*
Holliday, Mutations and epimutations in mammalian cells, Mutation Research, vol. 250, pp. 351–363, 1991.*
Cosgrove et al., Effects of sodium butyrate and 5–azacytidine on DNA methylation in human tumor cell lines: variable response to drug treatment and withdrawal, Biochim, Biophys. Acta, vol. 1087, pp. 80–86, 1990.*
Hopkin, K., "Move Over, Mutations: DNA Methylation May Drive Cancer, Too," The Journal of NIH Research, vol. 7, pp. 26–28, Jul. 1995.
Rouleau et al. (1992) *J. Biol. Chem.* 267:7368–7377.
Razin et al. (1984) *Biochim. Biophys. Acta.* 782:331–342.
Szyf et al. (1992) *J. Biol. Chem.* 267:12831–12836.
Ohtani–Fukita et al. (1993) *Oncogene* 8:1063–1067.
Feinberg et al. (1988) *Cancer Res.* 48:1159–1161.
Goelz et al. (1985) *Science* 228:187–190.
Feinberg and Vogelstein (1983) *Nature* 301:89–92.

(List continued on next page.)

Primary Examiner—Robert A. Schwartzman
Assistant Examiner—Andrew Wang
(74) Attorney, Agent, or Firm—Hale and Dorr LLP

(57) ABSTRACT

The present invention relates to the interplay between the level of DNA methyltransferase and demethylase activities, to the role of the interplay between these levels on the proliferative, differentiated, tumorigenic and homeostatic state of the cell, and to the DNA methyltransferase and demethylase as therapeutic targets. The invention further relates to a reduction of the level of DNA methylation through inhibitors and antagonist in order to inhibit the excessive activity or hypermethylation of DNA MeTase in cancer cells to induce the original cellular tumor suppressing program, to turn on alternative gene expression programs, to provide therapeutics directed at a nodal point of regulation of genetic information, and to modulate the general level of methylase and demethylase enzymatic activity of a cell to permit specific changes in the methylation pattern of a cell.

3 Claims, 15 Drawing Sheets

OTHER PUBLICATIONS

Agrawal (1992) *Trends in Biotech* 10:152.
Stepheneson et al. (1978) *Proc. Natl. Acad. Sci. U.S.A.* 75:285.
Leonetti et al. (1988) *Gene* 72:323.
Burch and Mahan (1991) *J. Clin. Invest.* 88:1190.
Jones et al. (1990) *Adv. in Cancer Res.* 54:1–23.
Yen et al. (1992) *Nucl. Acids. Res.* 9:2287–2291.
Zakut–Houri et al. (1983) *Nature* 306:594–597.
Ausubel et al., 1988, In Current Protocols in Molecular Biology. Wiley and Sons, New York.
Bestor et al., 1988, J. Mol. Biol. 203:971–983.
Bernards et al., 1989,. Proc. Natl. Acad. Sci. USA. 86:6474–6478.
Brandeis et al., 1993, BioEssays 15:709–713.
Ellis et al., 1991, Annu. Rev. Cell Biol. 7:663–698.
Maysinger et al., 1993, Neurochem Intl. 23: 123–129.
Freedman et al., 1974, Cell 3: 355–359.
Kumar et al., 1994, Nucl. Acids Res. 22:1–10.
Li et al., 1992, Cell 69:915–926.
Razin et al., 1980, Science 210:604–610.
Razin et al., 1991, Microbiol. Rev. 55:451–458.
Szyf, 1991, Biochem. Cell Biol. 69:764–767.
Szyf et al., 1985, J. Biol. Chem. 260:8653–8656.
Szyf et al., 1991, J. Biol. Chem. 266:10027–10030.
Szyf et al., 1989, Proc. Natl. Acad. Sci. USA 86: 6853–6857.
Szyf et al., 1990, Mol.Endocrinol. 4:1144–1152.
Wu et al., 1993, Proc. Natl. Acad Sci. USA 90:8891–8895.
Razin et al., 1985, In Biochemistry and Biology of DNA methylation, pp. 239–253, Razin et al., (Ed), Allan R. Liss, Inc. N.Y.
Yisraeli et al., 1985, In DNA methylation: Biochemistry and Biological significance, pp. 353–378, Razin et al.,(Ed), Springer–Verlag, N.Y.
Yisraeli et al., 1986, Cell 46:409–416.
Szyf, 1994, Trends in Pharm. Sci., 15:233–238.
Babiss et al., 1985, Science, 228:1099–1101.
Walker et al., 1984, J. National Cancer Institute, 73:877–882.
Kautiainen et al., 1986, J. Biol. Chem., 261:1594–1598.
Jones, 1985, Cell, 40:485–486.
Kaul et al., 1984, Eur. J. Cell Biol., 34:330–335.
Neubauer et al., 1989, British J. Haematol, 72:492–496.
Soultanas et al., 1993, J. Mol. Endocri., 11:191–200.
Peeters (Ed), 1985, 'Protides of the biological fluids', Pergamon Press, Oxford, England, pp. 521–524.

* cited by examiner

DNA MeTase and demethylase activities determine the pattern of methylation in tumor cells

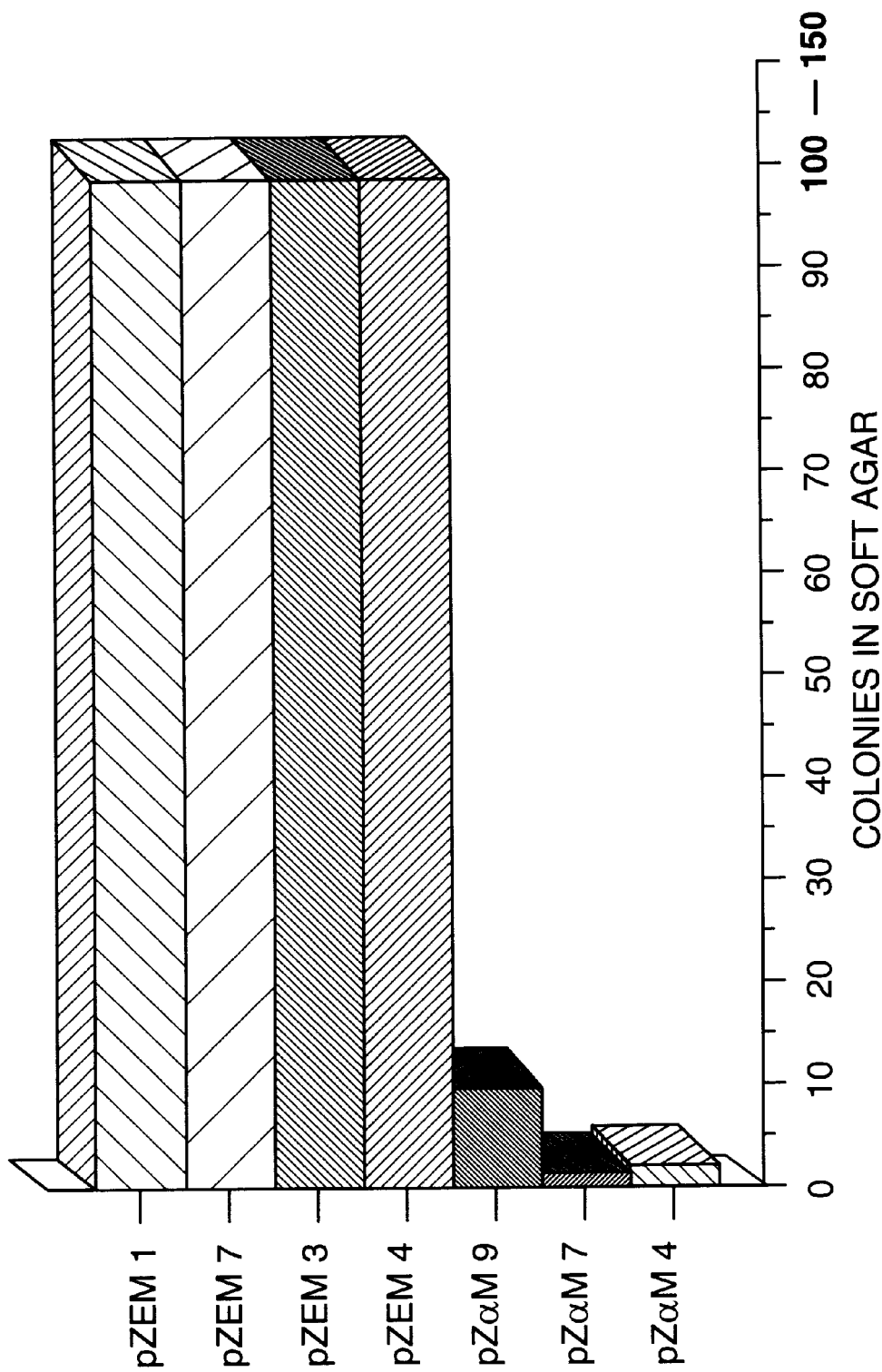

| Cell line injected | tumors | Neovascularization |
|---|---|---|
| Y1 | 6/6 | +++ |
| pZEM 4 | 5/5 | +++ |
| pZαM 4 | 1/6 | — |
| pZαM 7 | 2/6 | — |
| pZαM 9 | 2/6 | — |

INHIBITION OF DNA METHYLTRANSFERASE

TECHNICAL FIELD

The present invention relates to the interplay between the level of DNA methyltransferase and demethylase activities and to the role of this interplay on the proliferative, differentiated, tumorigenic and homeostatic state of the cell.

BACKGROUND ART

While transcription factors play a critical role in orchestrating the gene expression profiles of all organisms, other, "epigenetic" levels of information that encode the diversification program of an otherwise uniform. genetic content exist. Methylation of DNA is thought to be one such critical determinant of the diversification program (Razin et al., 1980, Science 210:604–610).

DNA methylation is a postreplicative covalent modification of DNA that is catalyzed by the DNA methyltransferase enzyme (MeTase) (Koomar et al., 1994, Nucl. Acids Res. 22:1–10; and Bestor et al., 1988, J. Mol. Biol. 203:971–983). In vertebrates, the cytosine moiety at a fraction of the CpG sequences is methylated (60–80%) in a nonrandom manner generating a pattern of methylation that is gene and tissue specific (Yisraeli and M. Szyf, 1985, In DNA methylation: Biochemistry and Biological significance, pp. 353–378, Razin et al., (Ed), Springer-Verlag, N.Y.). It is generally believed that methylation in regulatory regions of a gene is correlated with a repressed state of the gene (Yisraeli and Szyf, 1985, In DNA methylation: Biochemistry and Biological significance, pp. 353–378, Razin et al., (Ed), Springer-Verlag, N.Y.; and Razin et al., 1991, Microbiol. Rev. 55:451–458). Recent data suggest that DNA methylation can repress gene expression directly, by inhibiting binding of transcription factors to regulatory sequences or indirectly, by signaling the binding of methylated-DNA binding factors that direct repression of gene activity (Razin et al., 1991, Microbiol. Rev. 55:451–458). It is well established that regulated changes in the pattern of DNA methylation occur during development and cellular differentiation (Razin et al., 1991, Microbiol. Rev. 55:451–458; and Brandeis et al., 1993, Bioessays 13:709–713). Importantly, the critical role of DNA methylation in differentiation has recently been demonstrated (Li et al., 1992, Cell 69:915–926; and Szyf et al., 1992, J. Biol. Chem. 267:12831–12836). The pattern of methylation is maintained by the DNA MeTase at the time of replication and the level of DNA MeTase activity and gene expression is regulated with the growth state of different primary (Szyf et al., 1985, J. Biol. Chem. 260:8653–8656) and immortal cell lines (Szyf et al., 1991, J. Bol. Chem. 266:10027–10030). This regulated expression of DNA MeTase has been suggested to be critical for preserving the pattern of methylation.

Many lines of evidence have demonstrated aberrations in the pattern of methylation in transformed cells. For example, the 5' region of the retinoblastoma (Rb) and Wilms Tumor (WT) genes is methylated in a subset of tumors, and it has been suggested that inactivation of these genes in the respective tumors resulted from methylation rather than a mutation. In addition, the short arm of chromosome 11 in certain neoplastic cells is regionally hypermethylated. Several tumor suppressor genes are thought to be clustered in that area. If the level of DNA MeTase activity is critical for maintaining the pattern of methylation as has been suggested before (Szyf, 1991, Biochem. Cell Biol. 64:764–769), one possible explanation for this observed hypermethylation is the fact that DNA MeTase is dramatically induced in many tumor cells well beyond the change in the rate of DNA synthesis. The fact that the DNA MeTase promoter is activated by the Ras-AP-1 signalling pathway is consistent with the hypothesis that elevation of DNA MeTase activity and resulting hypermethylation in cancer is an effect of activation of the Ras-Jun signalling pathway.

It is clear that the pattern of methylation is established during development by sequential de novo methylation and demethylation events (Razin et al., 1991, Microbiol. Rev. 55:451–458; and Brandeis et al., 1993, Bioessays 13:709–713), the pattern being maintained in somatic cells. It is still unclear however, how methylation patterns are formed and maintained In vivo. Although a simple model has been proposed to explain the clonal inheritance of methylation patterns (Razin et al., 1980, Science 210:604–610), it does not explain how specific sites are de novo methylated or demethylated during the processes of differentiation and cellular transformation. Several lines of evidence suggest that factors, other than the state of methylation of the parental strand, are involved in targeting specific sites for methylation.

A similar mystery is how specific sites are demethylated during development and cellular transformation. One possible mechanism could be a passive loss of methylation, although an alternative hypothesis is that demethylation is accomplished by an independent enzymatic machinery.

Site specific loss of methylation is a well documented facet of vertebrate differentiation (Yisraeli and Szyf, 1985, In DNA methylation: Biochemistry and Biological significance, pp. 353–378, Razin et al., (Ed), Springer-Verlag, N.Y.; Razin et al., 1991, Microbiol. Rev. 55:451–458; and Brandeis et al., 1993, Bioessays 13:709–713). Whereas a loss of methylation could be accomplished by a passive process as described above, a series of observations have demonstrated that an active process of demethylation occurs in mammalian cells (see for example Yisraeli et al., 1986, Cell 46:409–416). Similar to de novo methylation, demethylation is directed by specific signals in the DNA sequence (Yisraeli et al., 1986, Cell 46:409–416; and see FIG. 1 herein for a model) and the probability of a site being methylated or demethylated is determined by the affinity of that site to either one of the DNA MeTase or demethylase. The affinity of each site to either enzyme is determined by the chromatin structure around the site (Szyf, 1991, Biochem. Cell Biol. 64:764–769).

In normal cells, the DNA methyltransferase is regulated and repressed, possibly by one of the tumor suppressors. An equilibrium between DNA methyl-transferase and demethylase activities maintains the methylation pattern. Methylated sites are indicated by (M) in FIG. 1. Inhibition of the repressor results in over-expression of the DNA MeTase (as indicated by the solid arrow) the genome becomes hypermethylated and tumorigenesis is initiated (tumor a). Another mechanism for up regulating the DNA methyltransferase is the activation of the Ras oncogenic pathway resulting in activation of Jun and over-expression of the DNA MeTase. However, it appears that the Ras pathway can activate the demethylase as well. The final pattern of methylation observed in this class of tumors will reflect both activities: hypermethylation (M) of sites that express low or medium affinity to the demethylase (sites 3,4,5) and hypomethylation of sites that are of high affinity but were methylated in the original cell (site number 6).

The lines of evidence that link cancer and hypermethylation are however still circumstantial. The critical question that remains to be answered is whether these changes in DNA methylation play a causal role in carcinogenesis.

The demonstration that hypermethylation correlates with carcinogenesis would be immensely useful since it could lead to methods of assessing the carcinogenic potential of cells as well as to therapeutic treatments of cancer patients. Of note, the fact that the level of DNA MeTase is limiting in mammalian cells is supported by the observation that a small elevation of cellular DNA MeTase levels by forced expression of an exogenously introduced DNA methyltransferase into NIH 3T3 cells results in a significant change in the methylation pattern (Wu et al., 1994, Proc. Natl. Acad Sci. USA 90:8891–8895).

In addition, if DNA methylation provides an important control over the state of differentiation of mammalian cells, then DNA methylation modifiers could serve as important therapeutic agents to alter the genetic program in a predictable manner and/or to restore an authentic program when it is disrupted by deregulation of DNA methylation.

Furthermore, the identification of the molecule responsible for the demethylase activity would be extremely useful for the same reasons as mentioned above, since the control of gene expression, of differentiation and cellular homeostasis appears dependent on the balance between the level of DNA MeTase and demethylase activities.

DISCLOSURE OF THE INVENTION

The present invention relates to the interplay between the level of DNA methyltransferase and demethylase activities and to the role of this interplay on the proliferative, differentiated, tumorigenic and homeostatic state of the cell. It relates also to the use of a reduction of a level of methylated cytosine in a CpG dinucleotide, for reversing a transformed state of a cell, for correcting an aberrant methylation pattern in DNA of a cell, or for changing a methylation pattern in DNA of a cell. DNA methyltransferase (DNA MeTase) inhibitors can, according to the present invention, be used to inhibit the excessive activity or hypermethylation of DNA MeTase in cancer cells and induce the original cellular tumor suppressing program. These inhibitors can also be used to turn on alternative gene expression programs. Specific DNA methyl-transferase antagonists can also provide therapeutics directed at a nodal point of regulation of genetic information. Moreover, the present invention relates to the pharmacological implications provided by the fact that specific changes in the methylation pattern of a cell can be obtained by modulating the general level of DNA MeTase and demethylase enzymatic activity of that cell. Therefore, silent genes can be activated through a change in the methylation pattern of the DNA. For example, β-thalassemia and sickle cell anemia can be treated by activating the β-globin gene following a change in its methylation pattern.

Based on the demonstration that over expression of DNA MeTase in NIH 3T3 cells resulted in cellular transformation (Wu et al., 1994, Proc. Natl. Acad Sci. USA 90:8891–8895), the present invention also relates to the DNA MeTase as a candidate target for anticancer therapy.

The present invention also relates to a recently purified demethylase activity from P19 cells and to the demonstration that this demethylase is induced in P19 cells transformed with RAS. Based on the increased hypomethylation in cancer, and the demonstration that the demethylase from P19 cells is induced by RAS, the present invention further relates to the demethylase as a candidate target for anticancer therapy. Furthermore, the demethylase activity could be extremely useful for the treatment of methylated DNA samples that are to be used in molecular analysis such as restriction mapping or cloning.

The present invention moreover relates to poly clonal or monoclonal antibodies directed against the DNA MeTase or demethylase, and to the use of such antibodies as therapeutic agents.

Moreover, the present invention relates to the use of DNA MeTase inhibitors, whether general or specific, as anticancer therapeutic agents.

In a preferred embodiment, the specific anticancer therapeutic agent is an antisense oligonucleotide, specific to DNA MeTase mRNA sequences. In a case wherein hypermethylation of tumor suppressor loci results in their repression, and demethylation results in the activation of genes encoding tumor stimulators thereby amounting to the induction of tumorigenesis, initiating antisense therapy against the DNA methyltransferase will result in a reduction in DNA MeTase activity, demethylation and reactivation of tumor suppressor genes. The products of these genes will inhibit the tumorigenic effect induced by the tumor stimulating genes and thus, the inhibition of hypermethylation will also inhibit the effects of hypomethylation.

In an other preferred embodiment, based on the crystal structure of the HhaI methylase (Kumar et al., 1994, Nucl. Acids Res. 22:1–10), presenting a detailed atomic structure of the DNA methyltransferase, it is now possible to rationally design highly specific antagonists. These novel antagonists can be potential candidates for anticancer and gene induction therapy. The potential advantage of anti DNA MeTase therapy over alternative chemotherapy approaches is that it targets a potential regulator of the cancer state rather than a nonspecific proliferative function. DNA MeTase inhibitors can thus provide a novel route of therapy directed at the regulation of the genetic information.

In yet another preferred embodiment, through the use of antisense therapy, reversal of the tumorigenic phenotype of the cell can be observed.

In the specification and appended claims the antisense designation should be interpreted as being a DNA or RNA molecule complementary to the MRNA or towards either of the two DNA strands against which it is targeted. This antisense can be a complementary full length version of the target sequence, a fragment thereof, or an oligonucleotide derived therefrom. This antisense can be obtained by biotechnological methods or synthesized chemically.

BRIEF DESCRIPTION OF THE DRAWINGS

FIG. 3A shows an autoradiogram of a representative TLC plate. The standard lane is of hemimethylated M13 DNA synthesized In vitro. FIG. 3B shows scintillation counts from spots corresponding to C and 5-methyl C. The values represent the means ± SEM;

In FIGS. 3C–3E, the open arrows indicate the position of demethylated fragments.

FIGS. 4A–4C shows the morphological transformation and reduced anchorage independent growth of Y1 cells transfected with pZαM. FIG. 4A shows a Phase contrast microscopy at ×200 magnification of living cultures of Y1 clonal transfectants with pZαM and Y1 controls. FIG. 4B shows pictures of phase contrast microscopy at ×10 of a 21 days soft agar assay of Y1 pZEM cells (clones 4 and 7) and Y1 pzαM transfectants (clones 4, 7 and 9). FIG. 4C shows an anchorage independent growth assay: Y1 pZEM (clones 4 and 7) and Y1 pZαM transfectants (clones 4, 7 and 9) after 21 days of growth in soft agar;

FIG. 5A illustrates the ability of two control lines (Y1 and pZEM4) and three YlpZαM transfectants (4, 7 and 9) to form tumors in LAF-1 mice, as well as the level of neovascularization in these tumors. FIG. 5B shows photographs of the homogenized tumors;

FIG. 6B shows the relative expression of the antisense normalized to that of the 18S signal;

FIG. 8A shows the content of nonmethylated cytosines in the dinucleotide sequence CpG as determined by a nearest neighbour analysis. FIG. 8B shows the effect of 5azaCdR on the viability of cells grown in low (1%) serum medium. FIG. 8C shows the anchorage independent growth in soft agar (in the absence of 5 azaCdR). FIG. 8D shows the number of colonies upon 5azaCdr treatment.

MODES FOR CARRYING OUT THE INVENTION

It has been previously demonstrated that forced expression of an "antisense" mRNA to the most 5' 600 bp or the DNA MeTase message (pZαM) can induce limited DNA demethylation in 10 T ½ cells (Szyf et al., 1992, J. Biol. Chem. 267:12831–12836). To directly test the hypothesis that the tumorigenicity of Y1 cells is controlled by the DNA MeTase, Y1 cells were transfected with either pZαM or a pZEM control.

I. Expression of Antisense to the DNA Methyltransferase Gene in Y1 Cells Results in Limited DNA Demethylation.

To directly inhibit DNA methylation in Y1 cells, the DNA MeTase antisense expression construct pZαM or a pZEM control vector (Szyf et al., 1992, J. Biol. Chem. 267:12831–12836) were introduced into Y1 cells by DNA mediated gene transfer. Y1 cells were maintained as monolayers in F-10 medium which was supplemented with 7.25% heat inactivated horse serum and 2.5% heat inactivated fetal calf serum (Immunocorp, Montreal). All other media and reagents for cell culture were obtained from GIBCO-BRL. Y1 cells ($1 \times 10^6$) were plated on a 150 mm dish (Nunc) 15 hours before transfection. The pZαM expression vector encoding the 5' of the murine DNA MeTase cDNA (10 ug) was cointroduced into Y1 cells with 1 ug of pUCSVneo as a selectable marker by DNA mediated gene transfer using the calcium phosphate protocol (Ausubel et al., 1988, In Current Protocols in Molecular Biology. Wiley and Sons, New York). Selection was initiated 48 hours after transfection by adding 0.25 mg/ml G418 (GIBCO-BRL) to the medium. G418 resistant cells were cloned in selective medium. For analysis of growth in soft agar, $1 \times 10^3$ cells were seeded in triplicate onto 30 mm dishes (Falcon) with 4 ml of F-10 medium containing 7.5% horse serum, 2.5% FCS, 0.25 mg/ml G418 (for transfectants) and 0.33% agar solution at 37° C. (Freedman et al.,1974, Cell 3: 355–359). Cells were fed with 2 ml of medium plus G418 every two days. Growth was scored as colonies containing >10 cells, 21 days after plating.

Figure 1:
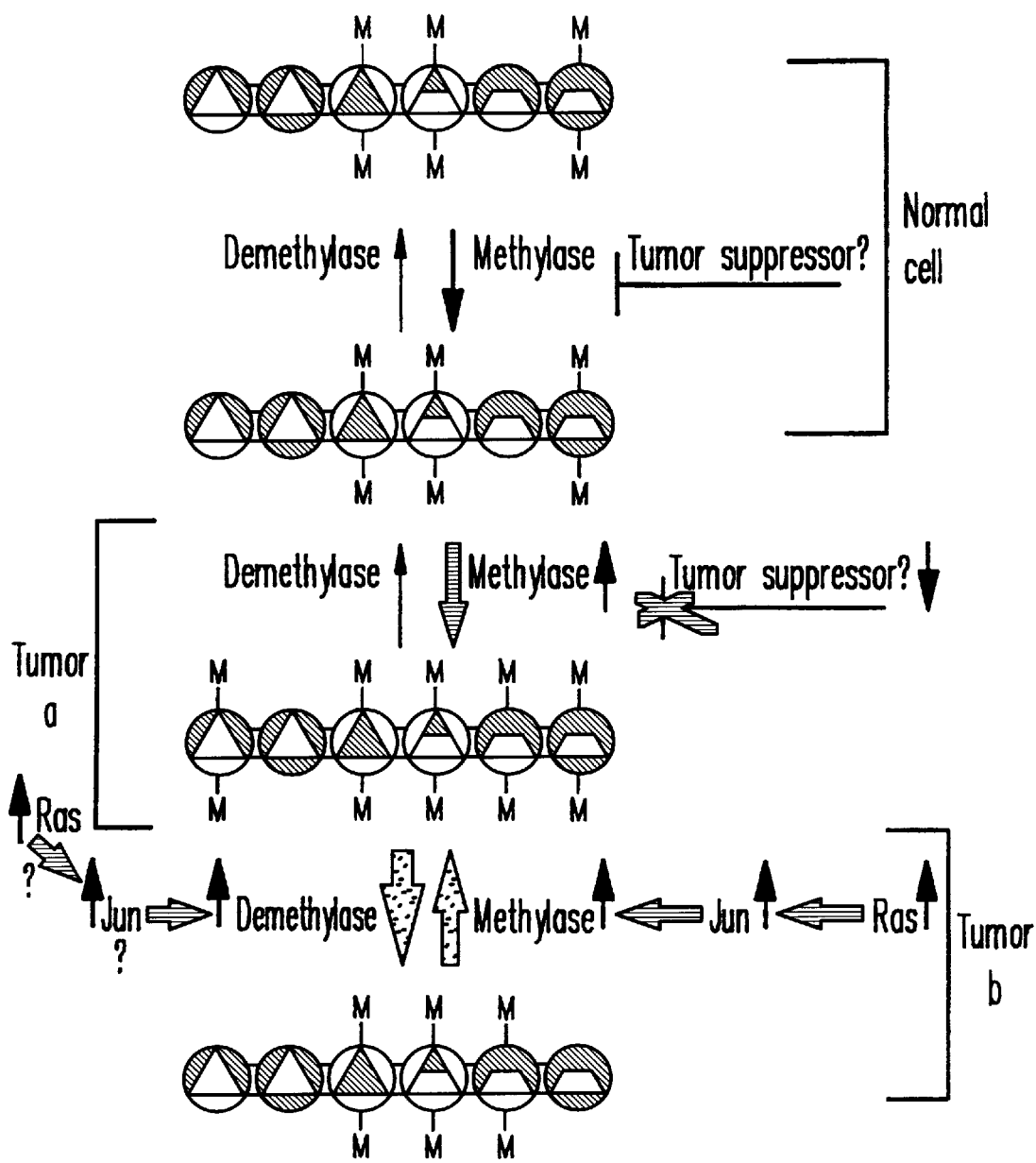
FIG. 1 illustrates that DNA MeTase and demethylase activities determine the pattern of DNA methylation in tumor cells.
Figure 2A:
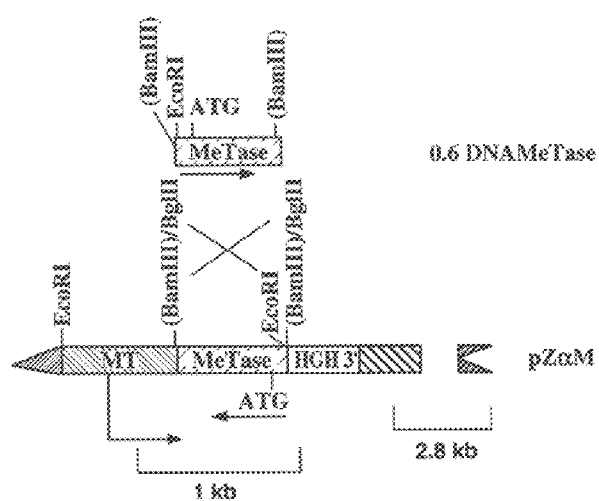
FIG. 2A illustrates plasmids pZEM and pZαM. The metallothionine (MT) promoter (shaded box), the human growth hormone 3' region (HGH) (open bar), and the MeTase cDNA sequences (hatched) are indicated.
Figure 2A:
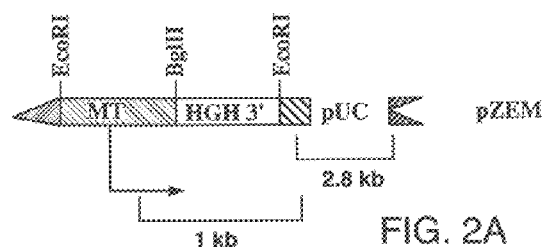
Figure 2B:
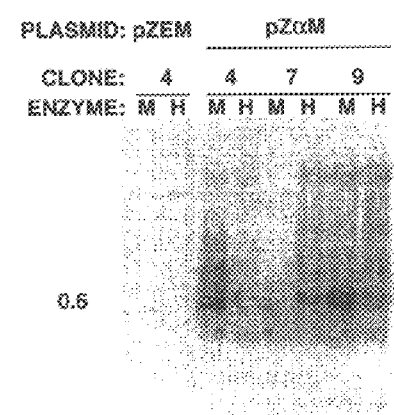
FIG. 2B shows a Southern blot analysis verifying the presence of the transfected plasmid in the transfectants.
Figure 2C:
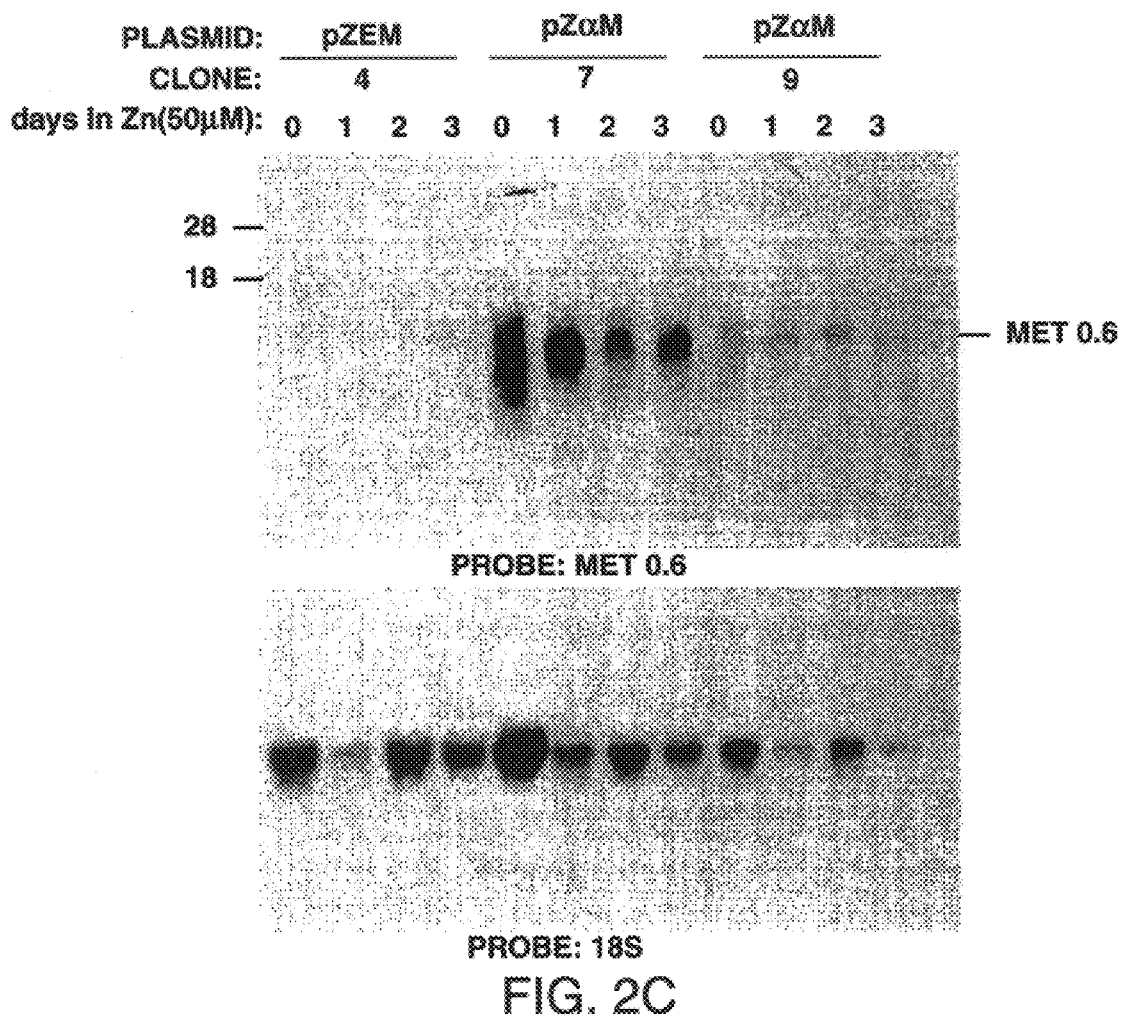
FIG. 2C shows a Northern blot analysis of the positive clones expressing the expected 1.3 kb chimeric mRNA. Total RNA (5 μg) was prepared from the three pZαM lines (7 and 9) and from the pZEM.

G418-resistant colonies were isolated and propagated for both constructs. To confirm that the transfectants bear the introduced construct, we prepared DNA from the transfectants and subjected it to digestion by either MspI or HpaII, Southern blot analysis and hybridization with a 32p labelled 0.6 kb DNA MeTase cDNA fragment (FIG. 2A). Preparation of genomic DNA and all other standard molecular biology manipulations, such as Labelling (using the random primer labelling kit from Boehringer Mannheim), were performed according to Ausubel et al., 1988, In Current Protocols in Molecular Biology. Wiley and Sons, New York). MspI and HpaII restriction enzymes (Boehringer Mannheim) were added to DNA at a concentration of 2.5 units/ug for 8 h at 37° C. Radionucleotides (3000 mCi/mmol) were purchased from Amersham. The results presented in FIG. 2B demonstrate that the three pZαM transfectants contained significant levels of the DNA MeTase cDNA sequence while the control transfectants were clean. To test whether the pZαM construct is expressed in the transfectants and whether the metallothionein promoter is functional in these cells, we cultured the transfectants with 50 uM of ZnS04, prepared RNA at different time points, subjected it to Northern blot analysis and hybridization with the 32p labelled MET 0.6 probe. Preparation of total cellular RNA, blotting RNA on to Hybond-N+ (Amersham), were performed according to Ausubel et al., (1988, In Current Protocols in Molecular Biology. Wiley and Sons, New York). As observed in FIG. 2C the transfectants 7 and 9 express substantial amounts of the MET 0.6 cDNA (~1.3 kb chimeric MRNA) even before induction with ZnS04. The ZnS04 induction increases the relative intensity of a 1.3 kb RNA hybridizing to MET 0.6 suggesting that ZnS04 induces the initiation of transcription from a discrete site but not the total expression of the antisense message (resulting in a smear in the non induced RNA samples). In subsequent experiments, induction of the transfectants with ZnSO4 was therefore not carried out.

To determine whether expression of antisense RNA to the DNA MeTase gene leads to a general reduction in the level of methylation of the genome, we resorted to "nearest neighbour" analysis using [α-32P]-dGTP as previously was performed. This assay enables the determination of the percentage of methylated cytosines residing in the dinucleotide sequence CpG (Razin et al., 1985, IN Biochemistry and Biology of DNA methylation, p. 239, Razin et al., (Ed), Allan R. Liss, Inc. N.Y.). Briefly, two ug of DNA were incubated at 37° C. for 15 minutes with 0.1 unit of DNAase, 2.5 of 32P-α-dGTP (3000 Ci/mmol from Amersham) and 2 units of Kornberg DNA polymerase (Boehringer) were then added and the reaction was incubated for an additional 25 minutes at 30° C. 50 ul of water were added and the nonincorporated nucleotides were removed by spinning through a microcon™ column (Amicon) at maximum speed for 30 seconds. The labelled DNA (20 ul) was digested with 70 ug of micrococal nuclease (Pharmacia) in the manufacturer's recommended buffer for 10 hours at 37° C. Equal amounts of radioactivity were loaded on TLC phosphocellulose plates (Merck) and the 3' mononucleotides were separated by chromatography in one dimension (iso-butyric acid: $H_2O:NH_4OH$ in the ratio 66:33:1). The chromatograms were exposed to XAR™ film (Eastman-Kodak) and the spots corresponding to cytosine and 5-methylcytosine were scraped and counted in a β-scintillation counter.

Figure 3A:
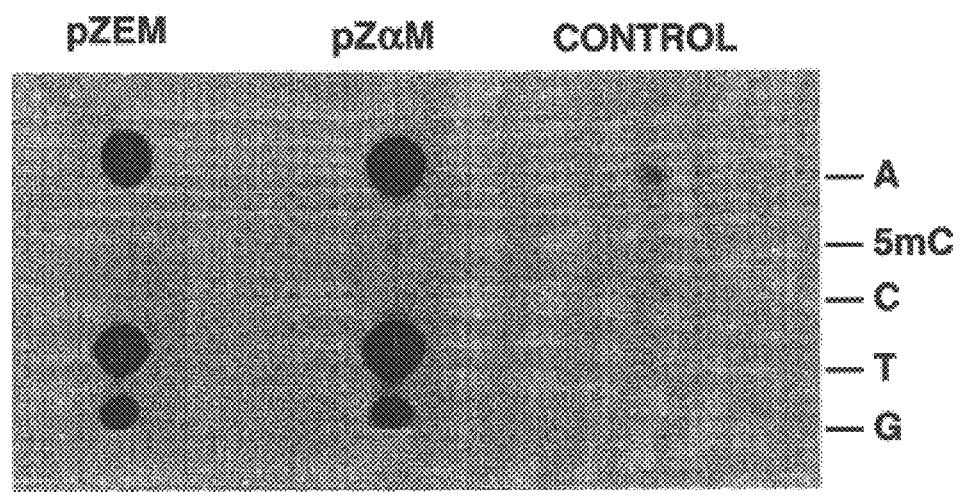
FIGS. 3A, 3B show the state of methylation of total genomic DNA in YlpZαM transfectants by nearest neighbour analysis of 2 ug DNA extracted from pZαM transfectant (4) and a pZEM control.
Figure 3B:
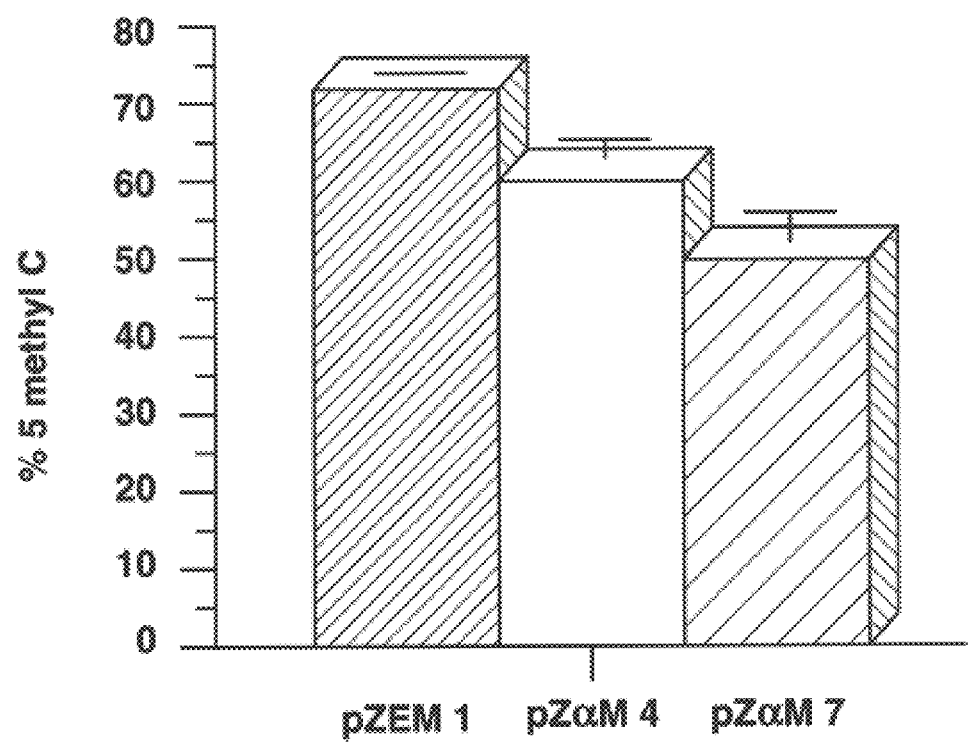

Transfectants and control DNAs were nicked with DNAaseI, nick translated with a single nucleotide [α-32P]-dGTP using DNA polymerase I and the labelled DNA was digested to 3' mononucleotide phosphates with micrococal nuclease which cleaves DNA 3 ' to the introduced α-32p. The [α-32P] labelled 5' neighbours of dGMP were separated by chromatography on a TLC plate, the resulting spots for dCMP and $dC^{met}MP$ were scraped and counted by liquid scintillation. The results of a triplicate experiment presented in FIG. 3A (sample autoradiogram) and B (graphic representation) suggest that a limited but significant reduction in the total level of DNA methylation (12% for transfectant number 4 and 22% for 7) occurred in transfectants expressing the pZαM construct when compared to the control line pZEM.

II. Demethylation of Specific Genes in Y1 pZαM Transfectants.

Figure 3C:
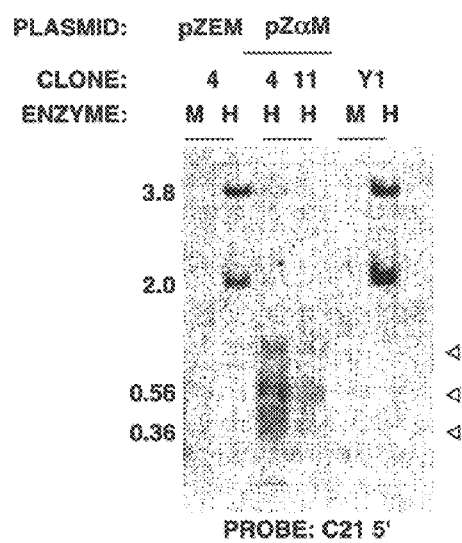
FIGS. 3C–3F. show Southern blot analyses following MspI/HpaII digestion (M/H) of the DNA illustrating, in YlpZαM transfectants, the state of methylation of specific genes: 3C: the C21 5' region, 3D: the C21 gene, 3E: the retinoblastoma (RB) gene and 3F: the p53 gene.
Figure 3D:
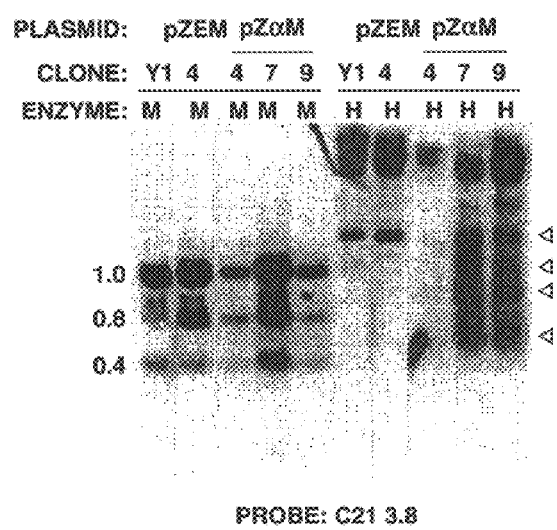

To further verify that expression of pZαM results in demethylation and to determine whether specific genes were demethylated, we resorted to a HpaII/MspI restriction enzyme analysis followed by Southern blotting and hybridization with specific gene probes. HpaII cleaves the sequence CCGG, a subset of the CpG dinucleotide sequences, only when the site is unmethylated while MspI will cleave the same sequence irrespective of its state of methylation. By comparing the pattern of HpaII cleavage of specific genes in cells expressing pZαM with that of the parental Y1 or cells harboring only the vector, it can be determined whether the genes are demethylated in the antisense transfectants. The state of methylation of the steroid 21-hydroxylase gene C21 (Szyf et al., 1989, Proc. Natl. Acad. Sci. USA 86: 6853–6857; and Szyf et al., 1990, Mol.Endocrinol. 4:1144–1152) was first analyzed. This gene is specifically expressed and hypomethylated in the adrenal cortex but is inactivated and hypermethylated in Y1 cells. It has been previously suggested that hypermethylation of C21 in Y1 cell is part of the transformation program that includes the shut down of certain differentiated functions. DNA prepared from Y1, pZαm and pZEM (Bernards et al., 1989,. Proc. Natl. Acad. Sci. USA. 86:6474–6478) transfectants was subjected to either MspI or HpaII digestion, Southern blot analysis and hybridization with a 0.36 kb Xba-BamHI fragment containing the enhancer and promoter regions of the C21 gene (see references Szyf et al., 1989, Proc. Natl. Acad. Sci. USA 86:6853–6857; and Szyf et al., 1990, Mol. Endocrinol. 4:1144–1152, for a physical map of the probe). This probe should detect 0.36 kb and 0.16 kb HpaII fragments when the promoter region is fully demethylated. The promoter and enhancer region is heavily methylated in Y1 cells and the pZEM transfectants as indicated by the presence of the higher molecular weight partial HpaII fragments at 3.8 and 2 kb and the absence of any lower molecular weight fragments (FIG. 3C). In contrast, the Y1 pZαM transfectants bear a partially demethylated C21 5' region as indicated by the relative diminution of the 3.8 and 2 kb fragments and the appearance of the fully demethylated faint bands at 0.36 kb as well as as the fact that HpaII cleavage yields partial fragments at 0.56 and ~1 kb indicating partial hypomethylation of sites upstream and downstream to the enhancer region (FIG. 3C). To determine whether hypomethylation was limited to the enhancer region or if it spreads throughout the C21 gene locus, a similar HpaII digestion and Southern blot transfer on different preparations of DNA extracted from Y1 cells was performed. DNA from a control pZEM (Bernards et al., 1989,. Proc. Natl. Acad. Sci. USA. 86: 6474–6478) transfectant and three pZαM antisense transfectants (FIG. 3D) was hybridized to the filter with a 3.8 kb BamHI fragment containing the body of the C21 gene and 3' sequences. Full demethylation of this region should yield a doublet at ~1 kb, a 0.8 kb fragment and a 0.4 kb fragment as well as a number of low molecular weight fragments at 0.1–0.2 kb. As observed in FIG. 3D the C21 locus is heavily methylated in Y1 cells as well as the control transfectant as indicated by the high molecular weight fragments above 23 kb. Only a faint band is present in the expected 1 kb molecular weight range as well as a partial at 1.9 kb (FIG. 3D). The DNA extracted from the antisense transfectants exhibits a relative diminution of the high molecular weight fragments and relative intensification of the partial fragment at 1.9 kb as well as the appearance of new partial fragments in the lower molecular weight range between 1 and 0.4 kb indicating partial hypomethylation at large number of HpaII sites contained in the 3' region of the C21 gene. The pattern of demethylation, indicated by the large number of partial HpaII fragments (FIG. 3D), is compatible with a general partial hypomethylation rather than a specific loss of methylation in a distinct region of the C21 gene.

To determine whether demethylation is limited to genes that are potentially expressible in Y1 cells such as the adrenal cortex-specific C21 gene or if the demethylation is widely spread in the genome, other genes such as the muscle specific MyoD gene as well as the hippocampus specific 5HT1A receptor gene were analysed, and both genes were shown to be hypomethylated. Another class of genes that might have undergone a specific hypomethylation includes the tumor suppressor genes. The state of methylation of two genes from this class, p53 and retinoblastoma (RB) which are both tumor suppressor genes involved in cell cycle regulation was therefore determined. Loss of either one of these gene products has been shown to lead to deregulation of the cell cycle and neoplasia.

Oligoprimers for the 5'region of the mouse p53 gene were selected from the published genomic sequence (Accession number: X01235) using the Primer selecting program (PC Gene™). The 5' primer corresponding to bases 154–172: 5'TLC GAA TCG GTT TLC ACCC 3' SEQ ID NO:1 and the 3' primer corresponding to bases 472–492, 5' GGA GGA TGA GGG CCT GAA TGC 3'SEQ ID NO:2, were added to an amplification reaction mixture containing 100 ng of mouse DNA (from C2C12 cells) using the incubation conditions recommended by the manufacturer (Amersham Hot tub™; 1.5 mM $MgCl_2$) and the DNA was amplified for 40 cycles of 2 minutes at 95° C., 2 minutes at 55° C. and 0.5 minutes at 72° C . The reaction products were separated on a low-melt agarose gel (BRL) and the band corresponding to the expected size was excised and extracted according to standard protocols (Ausubel et al., 1988, In Current Protocols in Molecular Biology, Wiley and Sons, New York).

Since the genomic sequence of the mouse RB gene was unavailable through Genbank, we reverse transcribed the retinoblastoma mRNA from 0.5 ug of total mouse RNA (from C2C12 cells) using random oligonucleotide primers (Boehringer) with Superscript™ reverse transcriptase (BRL) under conditions recommended by the manufacturer. The RB sequence was amplified from the reverse transcribed cDNA using oligonucleotides corresponding to bases 2–628 of the published cDNA (Bernards et al., 1989,. Proc. Natl. Acad. Sci. USA. 86:6474–6478). The oligoprimers used were 5' GGA CTG GGG TGA GGA CGG 3' SEQ ID NO:3 (1–18) and 5' TTT CAG TAG ATA ACG CAC TGC TGG 3' SEQ ID NO:4 (620–610). The amplification conditions were as described above.

Figure 3E:
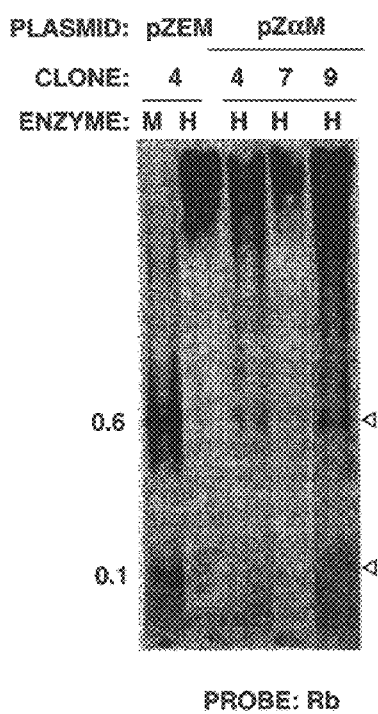

Using a probe to a 300 bp sequence from the 5' region of the mouse RB cDNA the level of methylation of this gene in Yl cells transfected with a control vector as well as the pZαM transfectants was determined (FIG. 3E). Cleavage of this region with HpaII yields 0.6 kb and 0.1 kb fragments (FIG. 3E). The RB locus is heavily methylated in the control cells as indicated by hybridization of the probe to high molecular weight fragments. This locus is partially hypomethylated in the pZαM transfectants as indicated by the relative diminution in the intensity of the high molecular weight fragments, the appearance of numerous partial fragments between 23 and 0.6 kb and the appearance of the demethylated fragments at 0.6 kb and ~0.1 kb.

Figure 3F:
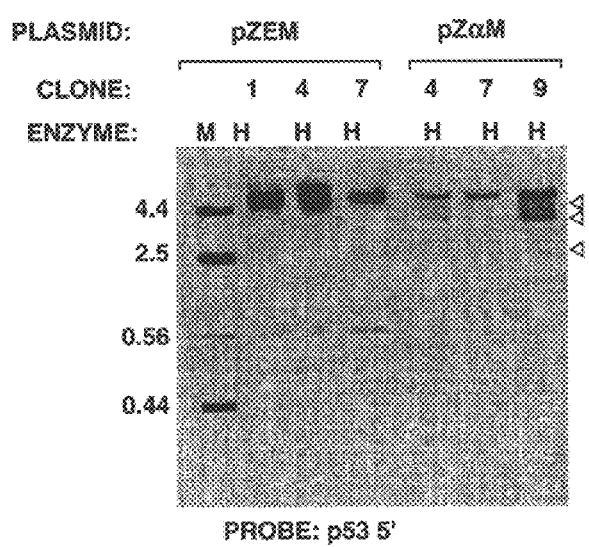

The p53 locus was studied using a 0.3 kb fragment from the 5' region 300 bp upstream to the initiation site as a probe (FIG. 3F). Cleavage of the p53 loci (two p53 genes are present in the mouse genome) with MspI yields fragments in the 4.4, 2.5, 0,56 and 0.44 kb molecular weight range (FIG. 3F, first lane). Cleavage of the control Yl pZEM transfectants shows that only the sites flanking the 0.56 kb fragments are demethylated in Yl cells. The rest of the locus is heavily methylated as indicated by the intensity of the signal at the >4.4 kb range (FIG. 3F, lanes 2–4). In comparison to the control transfectants the p53 gene is partially hypomethylated in Yl cells expressing an antisense message to the DNA MeTase as implied by the relative reduction in the intensity of the high molecular weight fragments above 4.4 kb and appearance of the 4.4 kb HpaII fragment, the partially cleaved HpaII fragment at 4 kb, the faint partial fragment around 3.5 kb and the faint fragment at 2.5 kb (FIG. 3F last three lanes). These results further substantiate the conclusion that expression of an antisense to the DNA MeTase results in a genome-wide partial hypomethylation. Neither of the genes studied demonstrates a distinct selectivity in demethylation.

EXAMPLE 1

Morphological Transformation and Loss of Anchorage Independent Growth of Yl Cells Expressing Antisense to the DNA MeTase.

Figure 4A:
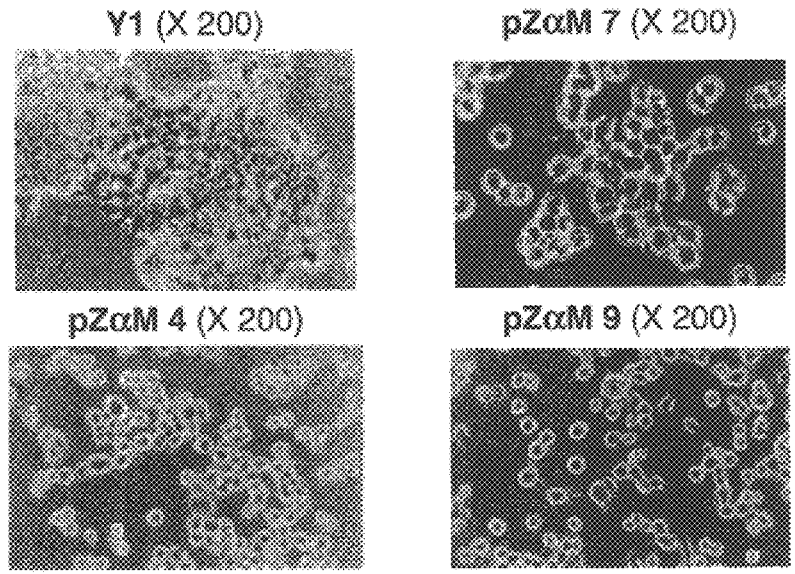
Figure 7A:
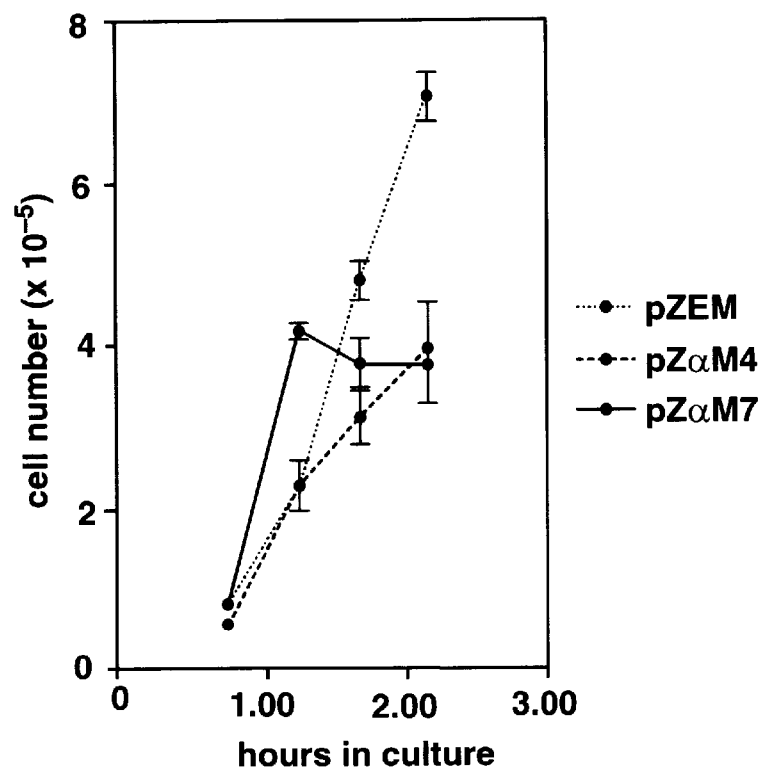
FIG. 7A shows a density restricted growth assay of Y1 pZαM relative to control pZEM transfectants.

To determine whether demethylation induced by the DNA MeTase antisense construct results in a change in the growth properties of cancer cells, the growth and morphological characteristics of the pZαM transfectants versus the controls we compared. To compare the growth curve of pZαM transfectants and controls, $5 \times 10^4$ Yl pZEM and pZαM transfectants (4 and 7) cells were plated in triplicate. The cells were harvested and counted at the indicated time points (FIG. 7A). The results of this experiment show that the antisense transfectants reach saturation density at lower concentrations than the control cells suggesting that the transfectants have reacquired "contact inhibition" which is one of the traits lost in cancer cells. The morphological properties of the Yl pZαM transfectants further support this conclusion (FIG. 4A). While control Yl and Yl pZEM cells exhibit limited contact inhibition and form multilayer foci, Yl pZαM transfectants exhibit a more rounded and distinct morphology and grow exclusively in monolayers (FIG. 4A).

Figure 4B:
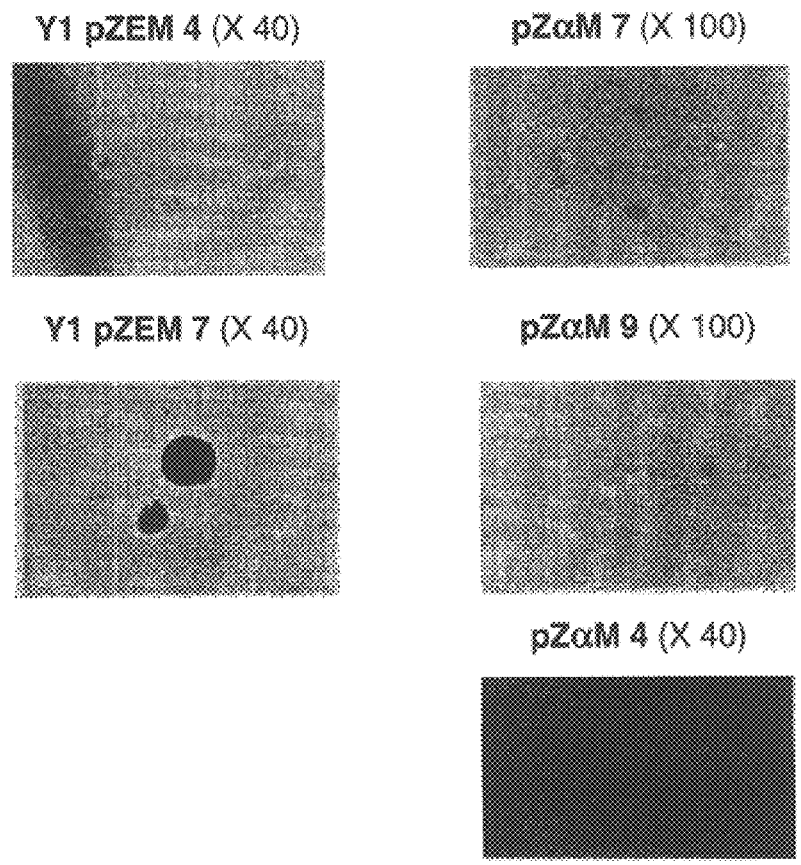

To determine whether the expression of antisense to the DNA MeTase results in reversal of the tumorigenic potential the ability of the transfectants to grow in an anchorage independent fashion, which is considered an indicator of tumorigenicity, was also determined. The Yl pZαM transfectants demonstrate an almost complete loss of ability to form colonies in soft agar, moreover the colonies that do form contain only a few cells as demonstrated in FIG. 4B. Growth on soft agar was quantified by visual examination and presented graphically in FIG. 4C.

These experiments demonstrate that inhibition of DNA methylation by expression of an antisense message to the DNA MeTase leads to loss of tumorigenicity In vitro.

EXAMPLE 2

Figures 5A, 5B:
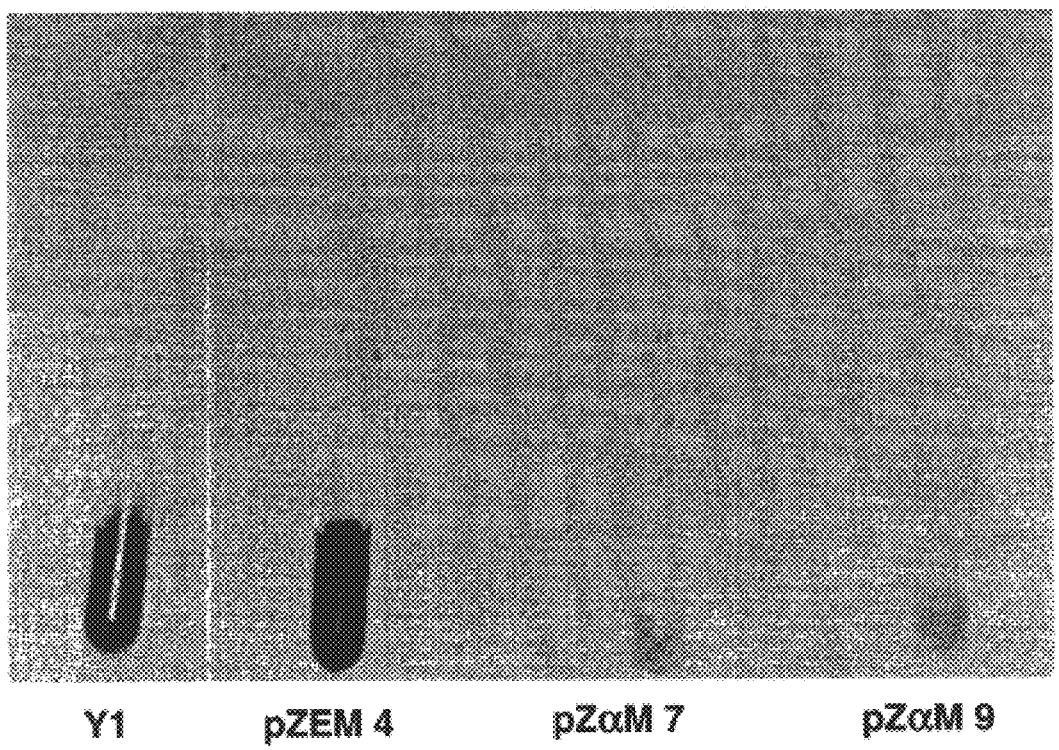
FIG. 5A–5B show the In vivo tumorigenicity of YlpZαM transfectants.

Yl Cells Expressing Antisense to the DNA MeTase Exhibit Decreased Tumorigenicity In vivo To determine whether demethylation can result in inhibition of tumorigenesis In vivo, LAF-1 mice (6–8 week old males) were injected subcutaneously (in the flank area) with $10^6$ cells for each of the Yl pZαM, Yl and Yl pZEM transfectants. Mice were monitored for the presence of tumors by daily palpation. Mice bearing tumors of greater than 1 cm in diameter were sacrificed by asphyxiation with $CO_2$, tumors were removed by dissection and homogenized in guanidium isothiocyanate. Mice that were tumor free were kept for ninety days and then sacrificed. RNA was prepared from the tumors by $CsCl_2$ density gradient centrifugation as described (Ausubel et al., 1988, In Current Protocols in Molecular Biology, Wiley and Sons, New York). While all the animals injected with Yl cells formed tumors two to three weeks post-injection, the rate of tumor formation in the animals injected with the pZαM transfectants was significantly lower (FIG. 5A; p>0.005).

Many lines of evidence suggest that angiogenic potential and metastatic potential of cell lines are directly related. The tumors that do arise from the pZαM transfectants exhibit very limited neovascularization (FIG. 5B) while tumors that formed in the animals that were injected with Yl cells or control transfectants were highly vascularized (FIG. 5B). This difference in neovascularization is indicated by the pale color of the homogenates of tumors removed from animals injected with Yl pZαM transfectants cells versus the very dark homogenates of tumors arising from control lines (Yl and YlpZEM; FIG. 5B).

Figure 6A:
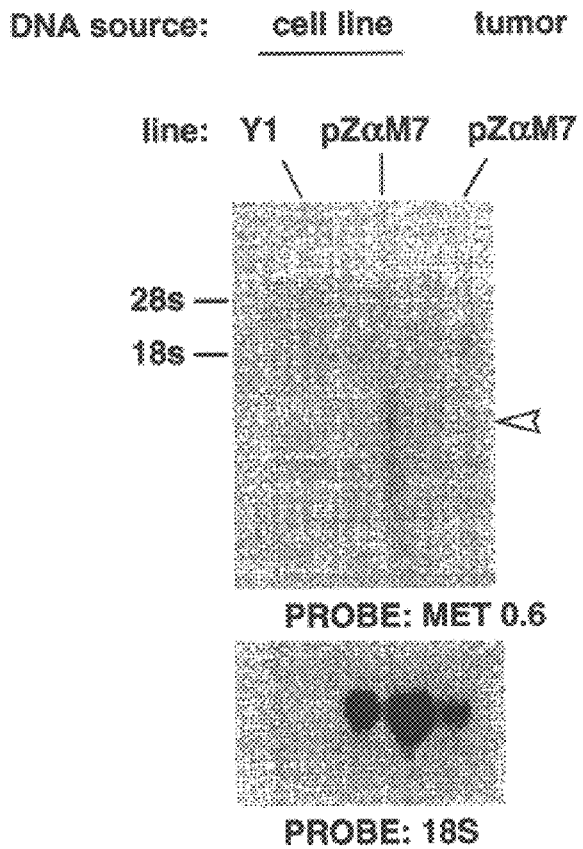
FIGS. 6A–6B show the loss of antisense expression in tumors derived from YlpZαM transfectants by Northern blot analysis. The 1.3 Kb antisense message is seen only in the original cell line pZαM 7 (dark arrow), and is undetectable in tumors arising from pZαM 7 or Y1 cell lines. A control for the amount of RNA loaded is also shown.
Figure 6B:
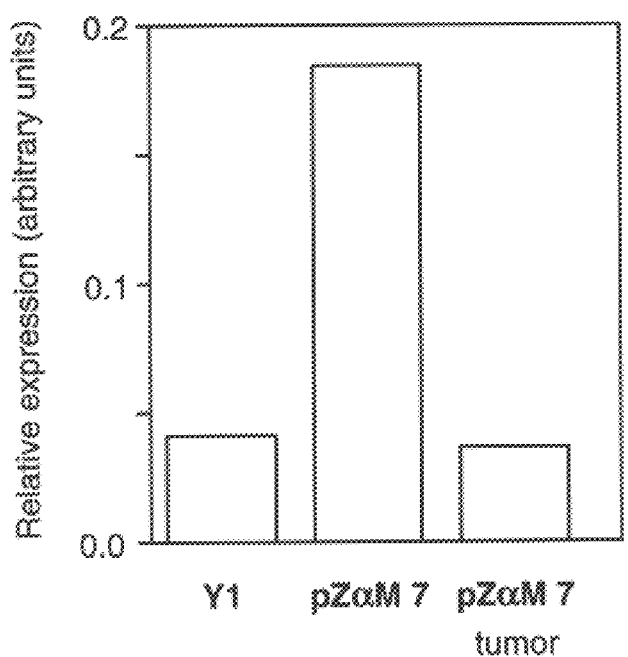

One possible explanation for the fact that a small number of tumors did form in animals injected with the pZαM transfectants is that they are derived from revertants that lost expression of the antisense to the DNA MeTase under the selective pressure In vivo. This hypothesis was tested with isolated RNA from a tumor arising from the YlpZαM transfectant, and compared to the level of expression of the 0.6 kb antisense message observed for the transfectant line In vitro. The isolated RNAs were subjected to Northern blot analysis and hybridization with a $^{32}$p labelled MET 0.6 fragment. The filter was stripped of its radioactivity and was rehybridized with a $^{32}$P labelled oligonucleotide probe for 18S rRNA (FIG. 6A) as previously described (Szyf et al., 1990, Mol. Endocrinol. 4:1144–1152). The autoradiograms were scanned and the level of expression of MET 0.6 was determined relative to the signal obtained with the 18S probe (FIG. 6B). The expression of the antisense message is significantly reduced in the tumors supporting the hypothesis that expression of an antisense message to the DNA MeTase is incompatible with tumorigenesis.

EXAMPLE 3

Figure 7B:
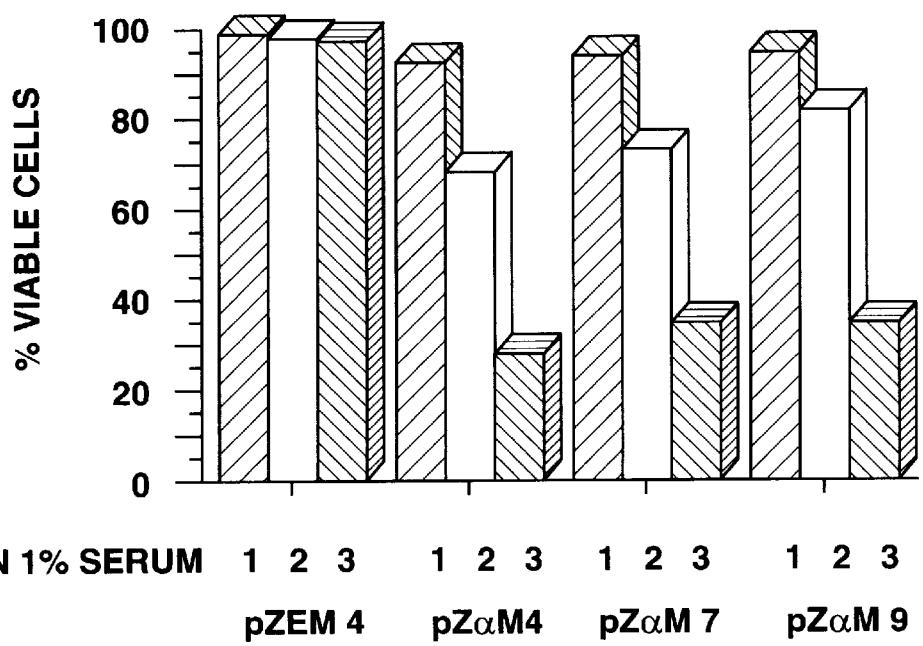
FIG. 7B shows the percentage of viable cells as determined using trypan blue staining following serum-deprivation (1% horse serum)

Expression of pZαM in Yl Cells Leads to an Induction of an Apoptotic Death Program upon Serum Deprivation Tumor cells exhibit limited dependence on serum and are usually capable of serum independent growth. Factors present in the serum are essential for the survival of many nontumorigenic cells. Several lines of evidence have recently suggested that the enhanced survivability of tumorigenic cells is associated with inhibition of programmed cell death. For example, the oncogene bc1–2 is not a stimulator of cell proliferation but rather causes inhibition of apoptosis. The tumor suppressor p53 can induce apoptosis in a human colon tumor derived line and certain chemotherapeutic agents have been shown to induce apoptosis in cancer cells. Since the pZαM transfectants appeared to demonstrate an enhanced dependence on serum and limited survivability under serum deprived conditions, the possibility that demethylation can induce an apoptotic program in Yl cells was analyzed. It was reasoned that as factors in the serum are known to act as survival factors for cells, an apoptotic program could be activated only when these factors are remove. To test whether pZαM transfectants undergo programmed cell death under serum deprived condition, the effects of serum starvation on these transfectants was studied. pZαM transfectants and control Yl pZEM transfectants ($3\times10^5$ per well) were plated in low serum medium (1% horse serum) in six well plates, harvested every 24 hours and tested for viability by trypan blue staining (FIG. 7B). While the control cells exhibited almost 100% viability up to 72 hours after transfer into serum deprived medium, the Yl pZαM cells showed up to 75% loss of viability at 48 hours (FIG. 7B).

Figures 7C, 7D:
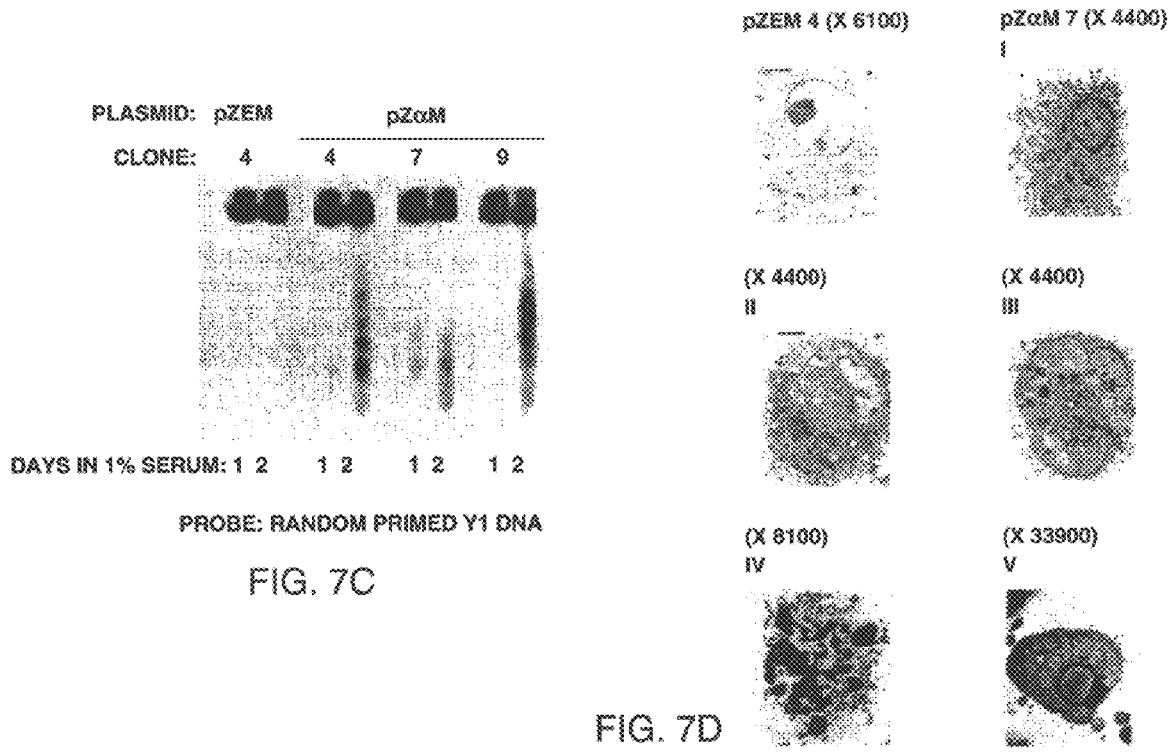
FIG. 7C shows a Southern analysis of total cellular DNA from the indicated transfectants following growth in 1% serum containing medium and harvested after 1 and 2 days. A 130 bp internucleosomal ladder characteristic of cells dying via apoptosis can be seen in the YlpZdM transfectants only.
FIG. 7D shows an electron microscopic analysis of various Y1 transfectants cell sections (I–V), following growth of the cells in 1% serum medium for 24 hours.
Figure 8A:
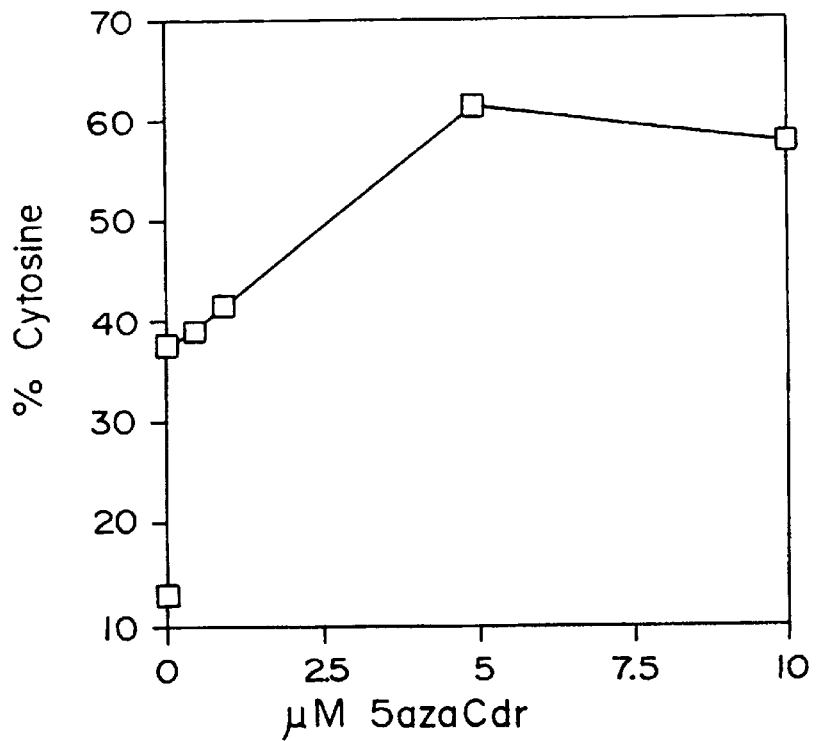
FIGS. 8A–8D shows the effect of 5 azaCdR-treatment (0–10 μM) of Y1 cells.
Figure 8B:
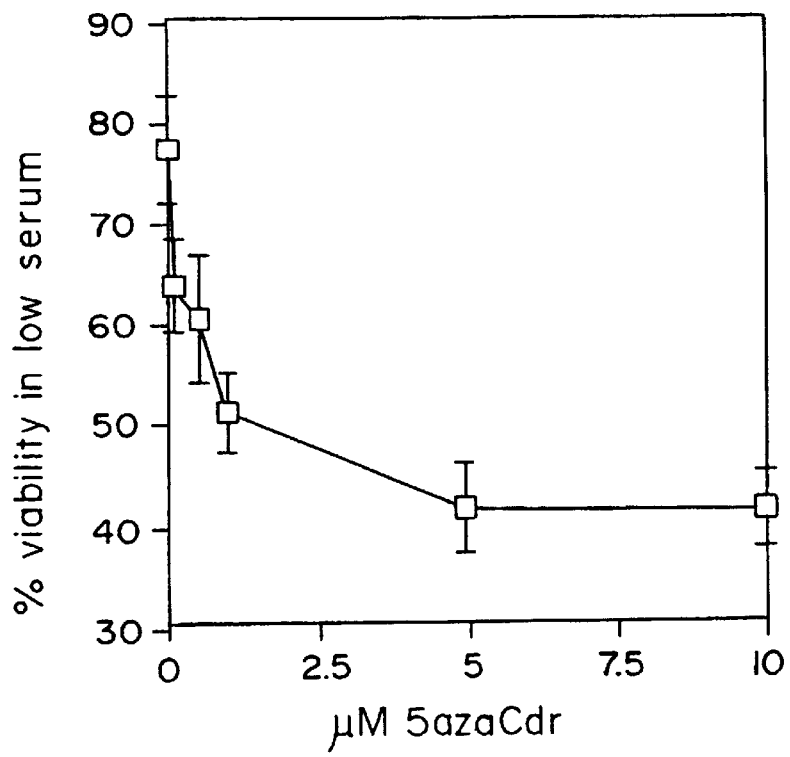
Figure 8C:
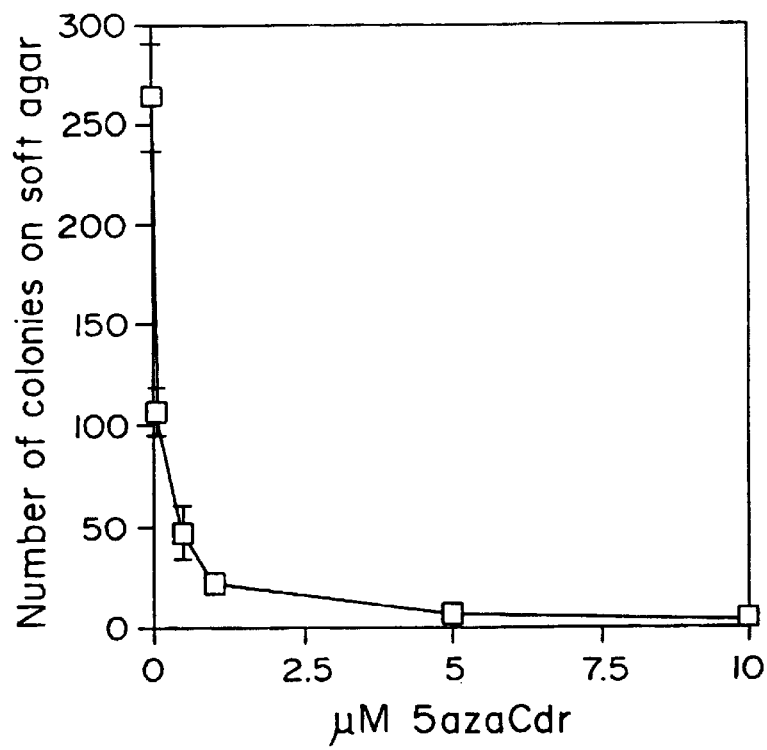
Figure 8D:
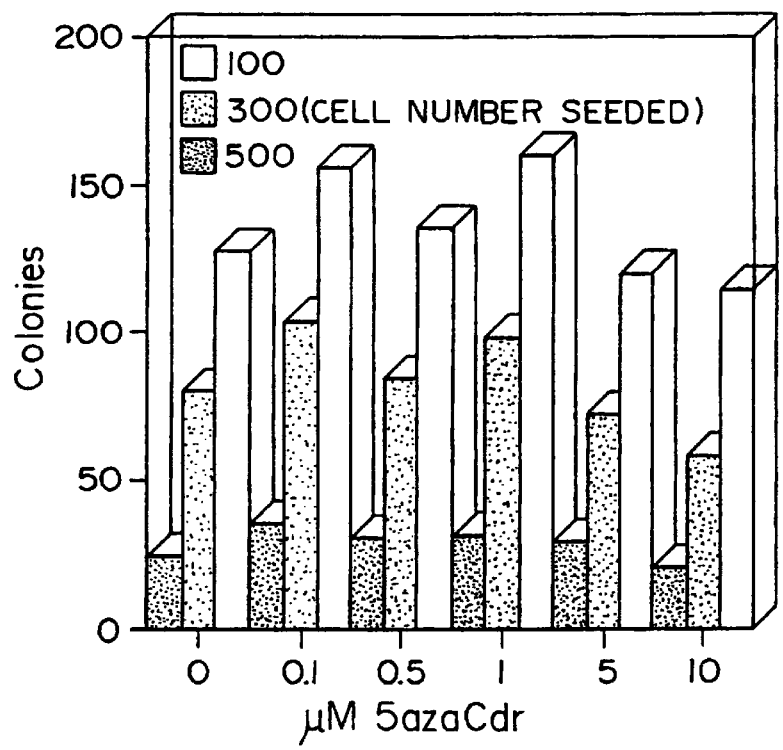

The rapid onset of death in Yl pZαM clones under serum deprived conditions suggests that an active process is involved. Several observable changes distinguish apoptosis from necrosis: apoptosis is an active process requiring de novo protein synthesis; apoptosis is associated with death of isolated cells, unlike necrosis where patches or areas of tissue die; cells dying by apoptosis do not elicit an immune response; and the most diagnostic feature of apoptosis is the pattern of degradation of the DNA from apoptotic cells (Ellis et al., 1991, Annu. Rev. Cell Biol. 7:663–698). DNA from cells dying by apoptosis generally exhibit a characteristic ladder when analyzed by gel electrophoresis because $Ca^{2+}$/$Mg^{2+}$ dependent endonucleases cleave the DNA at internucleosomal regions (Ellis et al., 1991, Annu. Rev. Cell Biol. 7:663–698). Although the appearance of the 180 bp internucleosomal ladder is a diagnostic feature of apoptotic death, other morphological changes such as chromatin condensation, cellular fragmentation; and formation of apoptotic bodies are generally considered to be earlier events in the apoptotic process and therefore also serve as useful markers. To test whether the serum deprived Yl pZαM cells were dying as a result of an activated apoptotic death program, cells were plated in starvation medium (1% horse serum) and harvested at 24 hour intervals. Total cellular DNA was isolated from the cells and was subjected to electrophoresis on a 1.5% agarose gel followed by transfer to nylon membrane and hybridization with random labeled Yl genomic DNA. After 48 hours in serum starved conditions, pZαM transfectants exhibit the characteristic 180 bp internucleosomal DNA ladder while the control pZEM transfectants show no apoptosis at this time point (FIG. 7C).

To determine whether cells expressing antisense to the DNA MeTase exhibit early morphological markers of apoptosis, cells were serum starved for 24 hours (2% horse serum), harvested and analyzed by electron microscopy. For electron microscopy, cells were fixed in glutaraldehyde (2.5%) in cacodylate buffer (0.1M) for one hour and further fixed in 1% osmium tetroxide. The samples were dehydrated in ascending alcohol concentrations and propylene oxide followed by embedding in Epon. Semithin sections (lum) were cut from blocks with an ultramicrotome, counterstained with uranil acetate and lead citrate. Samples were analyzed using a Philips 410 electron microscope (Maysinger et al., 1993, Neurochem Intl. 23: 123–129). FIG. 7D shows the electron micrographs of control Yl pZEM and Yl pZαM transfectants at various magnifications (I–V). The control cells have a fine uniform nuclear membrane whereas the pZαM cells exhibit the cardinal markers of apoptosis: condensation of chromatin and its margination at the nuclear periphery (panels I and II), chromatin condensation (panel II), nuclear fragmentation (panel III), formation of apoptotic bodies (panel V) and cellular fragmentation (panel IV). This set of experiments suggests that one possible mechanism through which demethylation can inhibit tumorigenesis is by activating programmed cell death. This is supported by data suggesting that cell death is triggered by an endonuclease activity (Ellis et al., 1991, Annu. Rev. Cell Biol. 7: 663–698). Thus, effects on the DNA methylation levels, can affect the pathway leading to apoptosis.

EXAMPLE 4

Treatment of Yl Cells with 5azaCdR $1\times10^5$ yl cells were plated in growth medium. Twenty-four hours after plating, the medium was replaced with fresh medium containing various concentrations (0–10 μM of 5 azaCdR (Sigma). The medium was removed and replaced with fresh medium containing 5 azaCdR every 12 h for a period of 72 h. Following 5 azaCdR treatment the cells were plated onto a six well dish in growth medium (100, 300, 500 cells per well) for cologinecity determinations, in soft agar for determining anchorage independent growth ($3\times10^3$ cells per well) and in low serum (1% horse serum) for five days to determine viability under serum deprived conditions. All of these assays were performed in the absence of 5 azaCdR.

As shown in FIG. 8, treatment of Yl cells with 5 azaCdR mimics the action of the expression of an antisense for MeTase. Indeed, treatment of Yl cells with 5 azaCdR is shown to increase the level of non-methylated cytosine (FIG. 8A), to decrease the viability of serum-starved cells (FIG. 8B), and finally to drastically inhibit the growth of Yl cells on soft agar (FIG. 8C–D). The effect of 5 azaCdR on Y1 cells was shown not to depend on the cell line per se since performing the same experiment under the same conditions but using Rb-human tumors and human small cell lung carcinoma cells gave similar results.

This set of experiment therefore suggests that 5 azaCdR can be successfully used as an anticancer agent, to alter the genetic program or to restore an authentic program disrupted by deregulation of DNA methylation.

Figure 9:
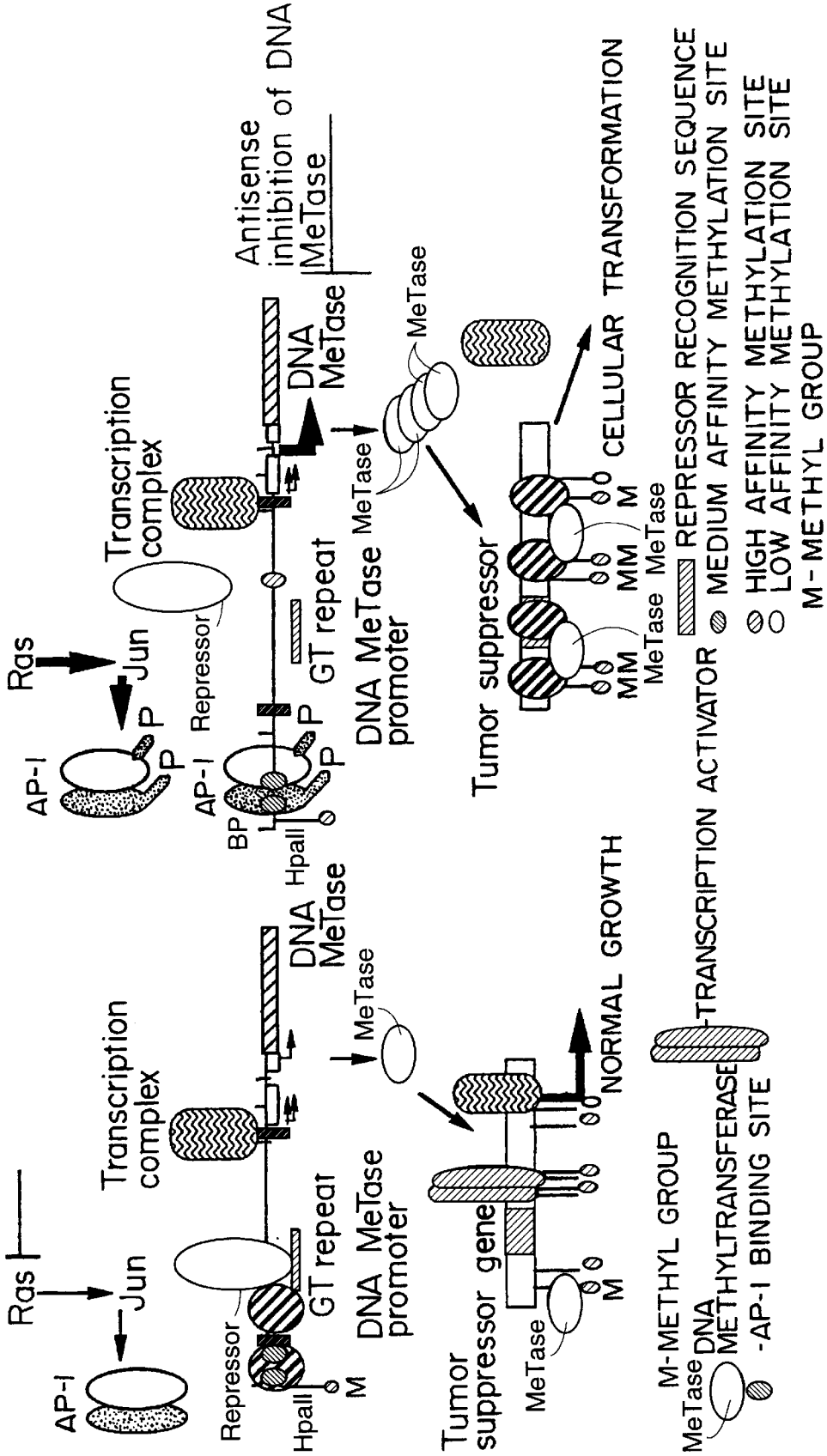
FIG. 9 illustrates the Regulation mechanism of the DNA MeTase promoter which determines DNA methylation patterns and cellular transformation.

The data presented herein, strongly support the hypothesis that hypermethylation plays a critical role in maintenance of the transformed state, and even predict that the increase in methylation is critical for the transformed state. The fact that the RAS signalling pathway has been shown to induce the activity of the DNA MeTase promoter provides us with a mechanism to explain this increase in the DNA methylation capacity of cancer cells (FIG. 9). It stands to reason therefore that the DNA MeTase is an important effector of the RAS signalling pathway.

Taken together, the data presented above, provide basic principles regarding the therapeutic implications of DNA methylation. First, because the level of DNA MeTase activity is one determinant of the pattern of DNA methylation, partial inhibition of DNA MeTase activity can result in a change in the methylation pattern. If aberrant hypermethylation in cancer cells is caused by over-expression of the DNA methyltransferase, then partial inhibition of methylation is expected to restore the original methylation pattern. Second, since this pattern is not exclusively determined by the DNA MeTase activity but is also defined by cis- and trans-acting signals at the gene site, a partial inhibition of DNA MeTase will result in a programmed change in gene expression rather than a chaotic transformation of the cell. Furthermore, DNA MeTase inhibitors can be used to induce a program that is latent in the cell.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

What is claimed is:

1. A method for reversing a tumorigenic state of a cell comprising administering an agent that reduces the level or activity of a DNA methyltransferase or increases the level or activity of a DNA dimethylase thereby reducing methylation of cytosine in a CpG dinucleotide in the cell, thereby correcting an aberrant methylation pattern in the DNA of the cell.

2. The method of claim 1, wherein the reduction of the level of methylated cytosine in a CpG dinudeotide is effected by inhibiting DNA methyltransferase activity.

3. The method of claim 1, wherein the reduction of the level of methylated cytosine in a CpG dinucleotide is effected by increasing demethylase activity.

* * * * *

UNITED STATES PATENT AND TRADEMARK OFFICE
CERTIFICATE OF CORRECTION

PATENT NO. : 6,184,211 B1
DATED : February 6, 2001
INVENTOR(S) : Moshe Szyf

It is certified that error appears in the above-identified patent and that said Letters Patent is hereby corrected as shown below:

Claim 2, column 16,
Line 31, "dinudeotide" should be -- dinucleotide --.

Signed and Sealed this

Second Day of October, 2001

Attest:

Nicholas P. Godici

NICHOLAS P. GODICI
Attesting Officer
Acting Director of the United States Patent and Trademark Office

UNITED STATES PATENT AND TRADEMARK OFFICE
CERTIFICATE OF CORRECTION

PATENT NO. : 6,184,211 B1
DATED : February 6, 2001
INVENTOR(S) : Moshe Szyf

It is certified that error appears in the above-identified patent and that said Letters Patent is hereby corrected as shown below:

Column 16, claim 2,
Line 31, "dinudeotide" should be -- dinucleotide --.

Signed and Sealed this

Eighth Day of January, 2002

Attest:

JAMES E. ROGAN
Attesting Officer
Director of the United States Patent and Trademark Office

UNITED STATES PATENT AND TRADEMARK OFFICE
CERTIFICATE OF CORRECTION

PATENT NO.   : 6,184,211 B1  Page 1 of 1
DATED        : February 6, 2001
INVENTOR(S)  : Moshe Szyf It is certified that error appears in the above-identified patent and that said Letters Patent is hereby corrected as shown below:

<u>Title page,</u>
Item [73], Assignee, should read as follows:
-- [73] Assignee: McGill University, Quebec (CA) --.

Signed and Sealed this

Thirteenth Day of August, 2002

Attest:

Attesting Officer

JAMES E. ROGAN
*Director of the United States Patent and Trademark Office*

```
                              SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:1:

TCCGAATCGG TTTCCACCC                                                    19

(2) INFORMATION FOR SEQ ID NO:2:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:2:

GGAGGATGAG GGCCTGAATG C                                                 21

(2) INFORMATION FOR SEQ ID NO:3:

(i) SEQUENCE CHARACTERISTICS:
         (A) LENGTH: 18 base pairs
         (B) TYPE: nucleic acid
         (C) STRANDEDNESS: single
```

```
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:3:

GGACTGGGGT GAGGACGG                                                           18

(2) INFORMATION FOR SEQ ID NO:4:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:4:

TTTCAGTAGA TAACGCACTG CTGG                                                    24
```